United States Patent
Seul et al.

(10) Patent No.: US 7,927,796 B2
(45) Date of Patent: *Apr. 19, 2011

(54) NUMBER CODING FOR IDENTIFICATION OF SUBTYPES OF CODED TYPES OF SOLID PHASE CARRIERS

(75) Inventors: Michael Seul, Fanwood, NJ (US); Enqing Tan, Kendall Park, NJ (US); Chiu Chau, Edison, NJ (US)

(73) Assignee: BioArray Solutions, Ltd., Warren, NJ (US)

( * ) Notice: Subject to any disclaimer, the term of this patent is extended or adjusted under 35 U.S.C. 154(b) by 1673 days.

This patent is subject to a terminal disclaimer.

(21) Appl. No.: 10/943,760

(22) Filed: Sep. 17, 2004

(65) Prior Publication Data

US 2005/0288870 A1    Dec. 29, 2005

Related U.S. Application Data

(60) Provisional application No. 60/504,294, filed on Sep. 18, 2003.

(51) Int. Cl.
*C12Q 1/68*     (2006.01)
*C12P 19/34*    (2006.01)
*C07H 21/04*    (2006.01)
*G01N 33/543*   (2006.01)
*G01N 15/06*    (2006.01)
*G01N 33/48*    (2006.01)

(52) U.S. Cl. .......... 435/6; 435/91.1; 536/24.3; 436/523; 422/68.1; 702/20

(58) Field of Classification Search .................. None
See application file for complete search history.

(56) References Cited

U.S. PATENT DOCUMENTS

| 5,567,627 | A | 10/1996 | Lehnen | |
| 6,908,737 | B2 * | 6/2005 | Ravkin et al. | 435/6 |
| 7,099,777 | B1 * | 8/2006 | Ghandour | 702/20 |
| 2004/0229269 | A1 * | 11/2004 | Hashmi et al. | 435/6 |

FOREIGN PATENT DOCUMENTS

| WO | WO99/36564 | 7/1999 |
| WO | WO 01/25510 | 4/2001 |
| WO | WO01/26038 A1 | 4/2001 |
| WO | WO02/079490 A2 | 10/2002 |

OTHER PUBLICATIONS

Michael et al., Randomly Ordered Addressable High-Density Optical Sensor Arrays, Anal. Chem. 1999, 70, 1242-1248.*

* cited by examiner

*Primary Examiner* — Marjorie Moran
*Assistant Examiner* — Larry D Riggs, II
(74) *Attorney, Agent, or Firm* — Womble Carlyle Sandridge & Rice PLLC (57) ABSTRACT

Disclosed is number coding of pairs ("doublets") or small sets ("multiplets") of solid phase carriers which provides distinguishable subtypes of a given type of such carriers, where each carrier type is distinguishable on the basis of a different code. Such number coding is useful for augmenting a coding system, such as a color code, and thereby effectively multiplying the number of "colors" (distinguishable sub-types). It can be applied, for example, to determine whether a sample is homozygous or heterozygous at a number of different sites for one of two different alleles, where the same color code is applied for each of the two alleles, and the alleles with the same color code are distinguished by knowing how many carriers are associated with molecules which detect each different allele.

8 Claims, 12 Drawing Sheets

Fig. 3
Peptide Encoding Strategy for Different Peptides

Fig. 9  Table 1

| Sample ID | Number of Shine Beads (With Assay Signals) | | | | Predicted Antibodies |
|---|---|---|---|---|---|
| | P6-Coupled Beads | P8-Coupled Beads | P12-Coupled Beads | total | |
| 1 | | | | 0 | negative sample |
| 2 | 50 | | | 50 | anti-P6 (+) |
| 3 | | 100 | | 100 | anti-P8 (+) |
| 4 | | | 200 | 200 | anti-P12 (+) |
| 5 | 50 | 100 | | 150 | anti-P6 & P8 (+) |
| 6 | 50 | | 200 | 250 | anti-P6 & P12 (+) |
| 7 | | 100 | 200 | 300 | anti-P8 & P12 (+) |
| 8 | 50 | 100 | 200 | 350 | anti-P6, P8, & P12 (+) |

Fig. 10
Table 2

| Bead Type | Peptide ID | # of Parts | # of Beads |
|---|---|---|---|
| A | P1,P5 | 1 | 30 |
| A | P1,P6 | 3 | 90 |
| A | P1,P7 | 6 | 180 |
| A | P1,P8 | 10 | 300 |
| B | P2,P5 | 3 | 90 |
| B | P2,P6 | 6 | 180 |
| B | P2,P7 | 10 | 300 |
| B | P2,P8 | 1 | 30 |
| C | P3,P5 | 6 | 180 |
| C | P3,P6 | 10 | 300 |
| C | P3,P7 | 1 | 30 |
| C | P3,P8 | 3 | 90 |
| D | P4,P5 | 10 | 300 |
| D | P4,P6 | 1 | 30 |
| D | P4,P7 | 3 | 90 |
| D | P4,P8 | 6 | 180 |

Fig. 11

Table 3A

| Sample ID | Number of Shine Beads (sub-total) | | | | Predicted Antibodies |
|---|---|---|---|---|---|
| | A | B | C | D | |
| 1 | 600 | 0 | 0 | 0 | P1(+) |
| 2 | 0 | 600 | 0 | 0 | P2(+) |
| 3 | 0 | 0 | 600 | 0 | P3(+) |
| 4 | 0 | 0 | 0 | 600 | P4(+) |
| 5 | 30 | 90 | 180 | 300 | P5(+) |
| 6 | 90 | 180 | 300 | 30 | P6(+) |
| 7 | 180 | 300 | 30 | 90 | P7(+) |
| 8 | 300 | 30 | 90 | 180 | P8(+) |
| 9 | 600 | 90 | 180 | 300 | P1(+),P5(+) |
| 10 | 600 | 180 | 300 | 30 | P1(+),P6(+) |
| 11 | 600 | 300 | 30 | 90 | P1(+),P7(+) |
| 12 | 600 | 30 | 90 | 180 | P1(+),P8(+) |
| 13 | 120 | 270 | 480 | 330 | P5(+),P6(+) |
| 14 | 210 | 390 | 210 | 390 | P5(+),P7(+) |
| 15 | 330 | 120 | 270 | 480 | P5(+),P8(+) |
| 16 | 270 | 480 | 330 | 120 | P6(+),P7(+) |
| 17 | 390 | 210 | 390 | 210 | P6(+),P8(+) |
| 18 | 480 | 330 | 120 | 270 | P7(+),P8(+) |

Fig. 12

Table 3B

| Sample ID | Peptide ID/ # of Bead With Signals/Type A | | | | | A-Total | Peptide ID/ # of Bead With Signals/Type B | | | | | B-Total |
|---|---|---|---|---|---|---|---|---|---|---|---|---|
| | P1,P5 | P1,P6 | P1,P7 | P1,P8 | | | P2,P5 | P2,P6 | P2,P7 | P2,P8 | | |
| 1 | 30 | 90 | 180 | 300 | | 600 | 0 | 0 | 0 | 0 | | 0 |
| 2 | 0 | 0 | 0 | 0 | | 0 | 90 | 180 | 300 | 30 | | 600 |
| 3 | 0 | 0 | 0 | 0 | | 0 | 0 | 0 | 0 | 0 | | 0 |
| 4 | 0 | 0 | 0 | 0 | | 0 | 0 | 0 | 0 | 0 | | 0 |
| 5 | 30 | 90 | 0 | 0 | | 30 | 90 | 0 | 0 | 0 | | 90 |
| 6 | 0 | 0 | 180 | 0 | | 90 | 0 | 180 | 0 | 0 | | 180 |
| 7 | 0 | 0 | 0 | 300 | | 180 | 0 | 0 | 300 | 0 | | 300 |
| 8 | 0 | 0 | 180 | 300 | | 300 | 90 | 0 | 0 | 30 | | 30 |
| 9 | 30 | 90 | 180 | 300 | | 600 | 0 | 0 | 0 | 0 | | 90 |
| 10 | 30 | 90 | 180 | 300 | | 600 | 0 | 180 | 0 | 0 | | 180 |
| 11 | 30 | 90 | 180 | 300 | | 600 | 0 | 0 | 300 | 0 | | 300 |
| 12 | 30 | 90 | 180 | 300 | | 600 | 0 | 0 | 0 | 30 | | 30 |
| 13 | 30 | 0 | 0 | 0 | | 120 | 90 | 180 | 0 | 0 | | 270 |
| 14 | 30 | 0 | 180 | 0 | | 210 | 90 | 0 | 300 | 0 | | 390 |
| 15 | 30 | 90 | 0 | 300 | | 330 | 0 | 180 | 0 | 30 | | 120 |
| 16 | 0 | 0 | 180 | 0 | | 270 | 0 | 180 | 0 | 0 | | 480 |
| 17 | 0 | 90 | 0 | 300 | | 390 | 0 | 180 | 300 | 30 | | 210 |
| 18 | 0 | 0 | 180 | 300 | | 480 | 0 | 0 | 300 | 30 | | 330 |

Fig. 13

Table 3C

| Sample ID | Peptide ID/ # of Bead With Signals/Type C | | | | | | C-Total | Peptide ID/ # of Bead With Signals/Type D | | | | | | D-Total |
|---|---|---|---|---|---|---|---|---|---|---|---|---|---|---|
| | P3,P5 | P3,P6 | P3,P7 | P3,P8 | | | | P4,P5 | P4,P6 | P4,P7 | P4,P8 | | | |
| 1 | 0 | 0 | 0 | 0 | | | 0 | 0 | 0 | 0 | 0 | | | 0 |
| 2 | 0 | 0 | 0 | 0 | | | 0 | 0 | 0 | 0 | 0 | | | 0 |
| 3 | 180 | 300 | 30 | 90 | | | 600 | 0 | 0 | 0 | 0 | | | 0 |
| 4 | 0 | 0 | 0 | 0 | | | 0 | 300 | 0 | 90 | 180 | | | 600 |
| 5 | 180 | 300 | 0 | 0 | | | 180 | 300 | 0 | 0 | 0 | | | 300 |
| 6 | 0 | 0 | 30 | 0 | | | 300 | 0 | 30 | 0 | 0 | | | 30 |
| 7 | 0 | 0 | 0 | 0 | | | 30 | 0 | 0 | 0 | 0 | | | 90 |
| 8 | 0 | 0 | 0 | 0 | | | 90 | 0 | 0 | 0 | 180 | | | 180 |
| 9 | 180 | 300 | 30 | 0 | | | 180 | 300 | 0 | 0 | 0 | | | 300 |
| 10 | 0 | 0 | 0 | 0 | | | 300 | 0 | 30 | 0 | 0 | | | 30 |
| 11 | 0 | 0 | 0 | 90 | | | 30 | 0 | 0 | 90 | 0 | | | 90 |
| 12 | 0 | 0 | 30 | 0 | | | 90 | 0 | 30 | 0 | 180 | | | 180 |
| 13 | 180 | 300 | 0 | 0 | | | 480 | 300 | 0 | 0 | 0 | | | 330 |
| 14 | 180 | 0 | 30 | 0 | | | 210 | 300 | 0 | 90 | 0 | | | 390 |
| 15 | 180 | 0 | 0 | 90 | | | 270 | 300 | 0 | 0 | 180 | | | 480 |
| 16 | 0 | 300 | 30 | 0 | | | 330 | 0 | 30 | 0 | 0 | | | 120 |
| 17 | 0 | 300 | 0 | 90 | | | 390 | 0 | 30 | 90 | 180 | | | 210 |
| 18 | 0 | 0 | 30 | 90 | | | 120 | 0 | 0 | 90 | 180 | | | 270 |

NUMBER CODING FOR IDENTIFICATION OF SUBTYPES OF CODED TYPES OF SOLID PHASE CARRIERS

RELATED APPLICATIONS

This application claims priority to U.S. Provisional Application No. 60/504,294, filed Sep. 18, 2003.

FIELD OF THE INVENTION

The invention is in the field of encoded carriers for chemical entities.

BACKGROUND

Solid phase carriers for multiplexed analysis of multiple analytes, preferably are encoded using one of several available color coding methods (see U.S. Ser. No. 09/448,420, filed Nov. 23, 1999, entitled "Color-Encoding and In-Situ Interrogation of Matrix-Coupled Chemical Compounds"; U.S. Ser. No. 10/348,165, filed Jan. 21, 2003, entitled "Method of Controlling Solute Loading of Polymer Microparticles," U.S. Pat. No. 4,499,052 "Apparatus for Distinguishing Multiple Subpopulations of Cells") to produce spectrally distinguishable carriers; or using chemical tagging methods such as those commonly employed for encoding of combinatorial libraries to produce carriers distinguishable by way of decoding these tags by one of several methods known in the art (see, e.g., U.S. Pat. No. 6,503,759 "Complex Combinatorial Chemical Libraries Encoded with Tags"). In applications of interest, solid phase carriers are functionalized to display chemical entities such as nucleic acid probes or protein receptors, each such entity being uniquely associated with a code and defining a carrier type. Preferably, the molecular analysis of multiple analytes is performed in accordance with the Random Encoded Array Detection (READ™) format, as described in U.S. application Ser. No. 10/204,799, filed on Aug. 23, 2002, entitled "Multianalyte Molecular Analysis Using Application-Specific Random Particle Arrays" using microparticles ("beads") as the solid phase carriers.

A method of encoding by providing multiple instances ("multiplicities") of each distinguishable type of carrier within a set of N such types has been described in connection with a flow cytometric multiplexed immunoassay format (See U.S. Pat. No. 5,567,627—Lehnen). Although Lehnen states that larger numbers of analytes may be analyzed with this method, the examples relate to small numbers, N, of analytes, where N ranges from 2 to 4.

However, the molecular analysis of multiple analytes, and particularly the analysis of nucleic acid sequences, generally must accommodate numbers of analytes in the range of tens of analytes, or about $10 \leq N \leq 100$. An example is the multiplexed analysis of the 25 mutations in the cystic fibrosis transmembrane regulator gene designated by the American College of Medical Genetics (ACMG) for pan-ethnic carrier screening, requiring at least 25 pairs of probes to discriminate normal and variant alleles.

To ensure an unambiguous decoding, application of the method in Lehnen for use in a method of encoding carriers requires a unique decomposition of N into summands, $m_k$, such that no partial sum obtained by adding two or more summands can be obtained in any other way of combining summands, and no summand is itself the sum of two or more of the other summands. For example, if N=10 analytes are to be displayed on uniquely coded carriers, one might select ten prime numbers in an attempt to construct a unique set of multiplicities as required by Lehnen, e.g.: $m_1=5$, $m_2=7$, $m_3=11$, $m_4=13$, $m_5=17$, $m_6=19$, $m_7=23$, $m_8=29$, $m_9=31$, $m_{10}=37$, only to discover that this prescription fails, even for this value of N=10, given that $m_1+m_4=m_2+m_3$ and other non-unique combinations, which can be seen. Therefore, the task of constructing a unique decomposition for any N represents a problem to which Lehnen does not provide a solution.

Additional difficulties arise when consideration is given to practical requirements in assay design. For example, in typical quantitative assays which may produce, for each of several types of constituent probes, signal intensities varying over a wide range, the respective mean signal intensities generally will not be known a priori. Thus, even in the case of only two different types of carriers, when the standard deviation of the assay signal produced by the multiple instances of the first type of probe is comparable to the difference in mean signal intensities of first and second types of probes, codes will be corrupted, decoding will be compromised and assay scores will be indeterminate. Assay signal intensities have been observed to vary by 10% to 30% about the mean over a specific carrier type.

Additional practical requirements place further constraints on practical codes. Thus, each $m_k$ is bounded from below as a result of placing confidence intervals on assay scores. As described in greater detail below, this constraint, the random encoded array (READ™) format or equivalent assay formats, requires minimal multiplicities in the range of 30-50 to ensure desirable confidence intervals on assay determinations. Each $m_k$ also is bounded from above by the fact that the total number of carriers, M, readily accommodated in a practical assay format and thus typically in the range of ~100 to ~10,000, is finite, where $M = \Sigma_{(k=1) \, to \, (k=N)} m_k$, implying an upper limit for each of the $m_k$. Further, in practice, the number of carriers of any given type contained in aliquots of suspension of nominally equal volumes will display a statistical variation, requiring that values of individual multiplicities be selected so as to differ from one another by at least several standard deviations about each mean, and thus not be spaced too closely. The methods described in Lehnen, therefore, do not enable multianalyte molecular analysis and also are not practical or desirable as a means of carrier encoding.

However, when number coding ("N-coding") is augmented by an additional code—such as chemical coding and specifically color coding ("C-coding")—and when applied to represent a finite, known number of outcomes for each of a multiplicity of probe types included in a multiplexed analysis, it is practical and desirable. In a multiplexed analysis of molecular analytes, N-coding permits the representation of a finite number of known or anticipated assay scores or outcomes for each of a multiplicity of types of probes or receptors included in the analysis. N-coding thus can be used to discriminate nucleic acid alleles by N-coded subtypes of carriers, each subtype displaying a probe matched to one of the known or anticipated alleles; specifically, N-coding can be used to discriminate normal and variant alleles by pairs of probes, one of these complementary to the normal ("wild-type", W) allele and represented by a multiplicity $m_w$, the other complementary to the variant ("V") allele and represented by a multiplicity $m_v$, where $m_v \neq m_w$ but both alleles share one color code. N-coding also can be used to discriminate epitopes by N-coded subtypes of carriers, each subtype displaying a receptor capable of binding to one of the known or anticipated epitopes of a ligand of interest, all such epitopes or ligands sharing one color code.

SUMMARY OF THE INVENTION

Number coding of pairs ("doublets") or small sets ("multiplets") of solid phase carriers provides distinguishable subtypes of a given type of such carriers, where each carrier type is distinguishable on the basis of a C-code. Such number coding is useful for augmenting a coding system, such as a color code, and thereby effectively multiplying the number of "colors" (distinguishable sub-types). It can be applied advantageously, for example, in multiplexed nucleic acid or protein analysis.

In one embodiment, members of a pair of probes are encoded by N-coding of solid phase carriers of the same color, but each of several such different pairs of probes will be associated with a carrier type of a different color. This embodiment is useful, for example, in multiplexed mutation analysis, where a color code can be augmented (effectively doubled) by N-coding carriers displaying pairs of probes, where the pair members are complementary to, respectively, a wild-type and variant allele.

In another embodiment, sets of probes complementary, for example, to a polymorphic region and to each of the four possible bases at a designated polymorphic position within the region, are encoded by N-coding of solid phase carriers of the same color, and each of several such different sets of probes will be associated with a carrier type of a different color.

In yet another embodiment, where, for example, there are multiple epitopes associated with a particular antigen, or where one merely wishes to increase the available coding, proteins (peptides) representing epitopes can be associated with a solid phase carrier and used to screen biological samples for reactive proteins or antibodies. This may be used, for example, where pairs or small sets of epitopes are associated with a particular antigen. In such case, the C-coding can be augmented by N-coding of solid phase carriers of the same color, where such a carrier subset carries the pairs or set of proteins corresponding to such pairs or sets of epitopes, as applicable.

The solid phase carriers preferably are microparticles which are assembled into planar arrays of particles on a substrate for use in the Random Encoded Array Detection (READ™) format of analysis, as disclosed in Ser. No. 10/032,657, filed Dec. 28, 2001, entitled "Multianalyte Molecular Analysis Using Application-Specific Random Particle Arrays" (incorporated by reference).

The methods herein are particularly useful in applications requiring, for each analyte, the determination of one among only a finite number of possible assay scores. Specifically, N-coding of pairs of solid phase carriers is practical because only a small number of carrier subtypes, and in the case of mutation analysis only two carrier subtypes, need be distinguished, and a unique code is trivially available.

DETAILED DESCRIPTION

N-Coding of Pairs ("Doublets": Mutation Analysis and Carrier Screening—In the multiplexed analysis of mutations, a pair of probes is provided for each mutation of interest, a first probe designed to identify the "Wild-Type" ("W") and a second probe designed to identify the "Variant" ("V"). Identification may invoke hybridization (as disclosed in U.S. application Ser. No. 10/847,046, filed May 17, 2004 "Hybridization-Mediated Analysis of Polymorphisms (hMAP)," both being incorporated herein by reference) or elongation (as disclosed in U.S. application Ser. No. 10/271,602, filed Oct. 15, 2002 entitled "Multiplexed Analysis of Polymorphic Loci by Concurrent Interrogation and Enzyme-Mediated Detection," incorporated herein by reference).

For every type of C-coded carrier, a number $w:=n_C^W$, of carriers displaying the W-probe, and a number $v:=n_C^V$ (where $n_C^V \neq n_C^W$) of carriers displaying the V-probe are provided. $n_C^W$ and $n_C^V$ are selected so as to differ by a quantity $\Delta n_C$, which is sufficiently large to ensure that an unambiguous call can be made in view of the practical considerations and requirements discussed above. The selection criterion for $n_C^W$ and $n_C^V$ is discussed in greater detail below.

Each pair of probes can encounter only three possible scenarios: the W allele, the V allele or a heterozygous (H) target. The actual outcome is determined by "counting, comparing and (optionally) confirming" as follows:

---

Count the number of carriers, $p := n_c+$, (of, e.g., type C)
which score positive, as determined from the intensity of signal
recorded after completion of an assay designed to detect the presence
of the W and/or V form of the subsequence of interest;
Count the number of carriers, $n := n_c-$, (of type C) which -continued

```
score negative;
Compare:
    IF:
        p/w ~ 1: THEN: W-allele;
        Confirm: n/v ~ 1;
    IF NOT, THEN IF
        p/v ~ 1: THEN: V-allele;
        Confirm: n/w ~ 1;
    IF NOT, THEN IF
        p/(w+v) ~ 1: THEN: H;
        Confirm: n/(w+v) ~ 0;
```

N-Coding of Multiplets: Polymorphisms and Antibody/Epitope Pairs

The N-coding system also could be used to detect single-nucleotide polymorphisms (SNPs). In such case, for example using eMAP™ detection, one would generate four different sets of probes, each complementary to the subsequence of interest but distinguished in that each different set would carry, at the 3' terminal probe position juxtaposed to the SNP site, one of four different nucleotides: A, C, G or T. Each set of probes would be attached to a carrier to form a carrier subtype, and there would be different numbers of each such subtype. The possible outcomes in such case would multiply to one positive for each of a possible four, or any combination of two positives for heterozygotes.

N-coding also could be used in assays for detecting the presence, in a sample, of antibodies capable of binding to peptides displayed on beads, or, in the reverse situation, for detecting peptides in a sample where the antibodies are displayed on beads. In such case, N-coding could be used for increasing the number of available codes, where, for example, color coding is used to discriminate among peptide-antibody combinations. That is, certain combinations can be encoded using carriers of the same color, by N-coding of such same-colored carriers to discriminate among such different combinations. An assay for detecting antibodies can be of particular utility for detecting auto-antibodies in a patient, in support of a diagnosis of autoimmune disease.

N-coding is useful when beads of a single color are employed, but are functionalized to display three different peptides to detect antibodies in a sample directed against one or more of the peptides, each peptide representing one specific epitope of the cognate antigen. Different numbers of beads displaying each of the three peptides would be pooled; i.e., X beads display peptide P1, Y beads display peptide P2, and Z display peptide P3. The pooled beads are then placed in contact with a sample which may contain antibodies against one or more of the peptides P1, P2 or P3. The sample is removed, and the beads are exposed to a labeled, secondary detection antibody which binds to any antibodies bound to the peptides on the beads (e.g., a goat anti-human antibody, if the sample is human); the assay signals are then recorded. The assay would have been first calibrated so that differences in relative signal can be correlated with numbers of labeled beads; i.e., one would be able to determine, based on the relative signal, whether X, Y, Z or a combination or sub-combination of X, Y and Z beads generated a signal, indicating they had bound to antibodies in the sample. For example, the N-coding design in Table 2A may be used. Decoding the signal, therefore, indicates which specific epitope (or epitopes, if the signal indicates that a combination or subcombination of X, Y and Z beads generated a signal) were recognized by antibodies in the sample. This will permit classification of autoantibodies into subtypes for each autoantigen.

This assay system would be adequate where one was detecting relatively small numbers of different antibodies, and using numbers of beads where X, Y and Z are widely different. As noted above, N, the total number of beads, must have a unique decomposition, and the larger the numbers of peptides P1 . . . Px, the more difficult it is to construct such a unique decomposition.

Figure 3:
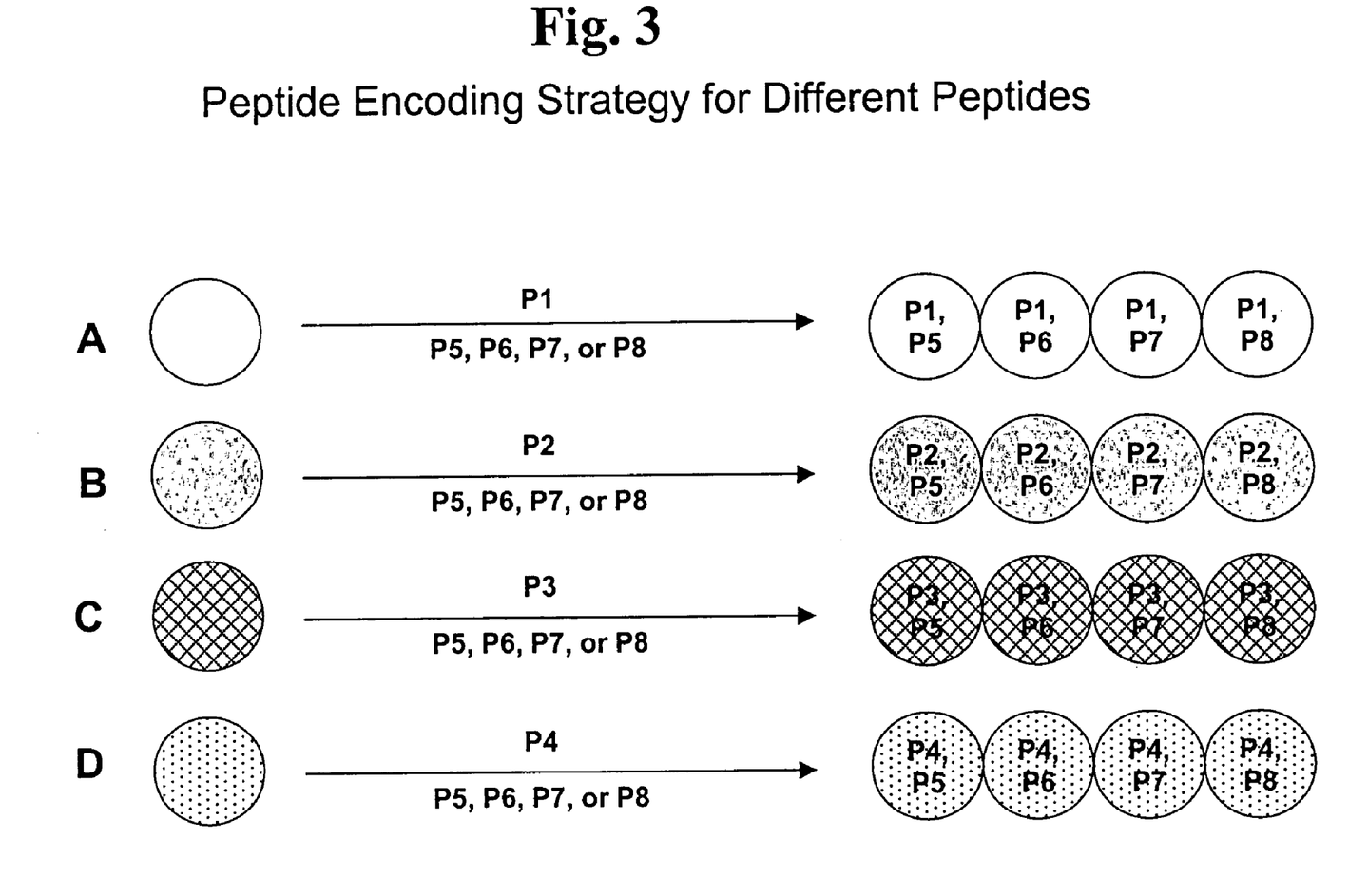
FIG. 3 depicts a coding system with four different C-codes ("colors") to encode bead types, for use in detecting antibodies against eight different peptides (P1 to P8).
Figure 4:
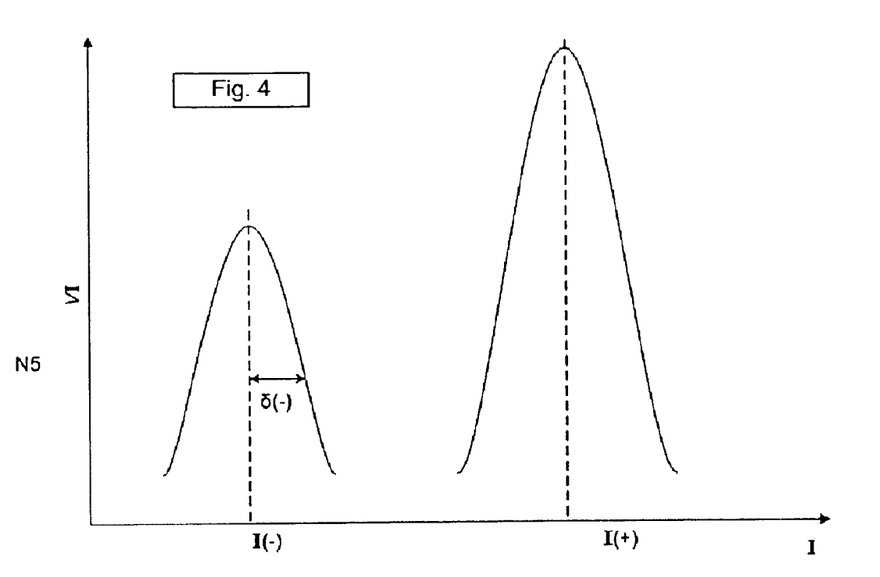
FIG. 4 depicts a histogram showing the number of beads displaying a certain intensity as a function of intensity, for detection of the "V" and "W" alleles using different numbers of carriers displaying probes which bind to the V or the W alleles. In the preferred case, the histogram has two distinct, non-overlapping peaks.

This assay system could also be used where a population of beads has uniquely encoded (e.g., C-coded) populations, N-coding can be enhanced to distinguish among a number of particles exceeding the number of available C-codes. For example, as shown in FIG. 3, four C-coded bead populations are each associated with, respectively, proteins or peptides P1, P2, P3 and P4, and members of each bead type also are associated with proteins or peptides P5, P6, P7 and P8. It may be advantageous to have multiple peptides attached to beads in this manner, if one is mapping non-linear epitopes, as combinations of epitopes may, when attached to the beads, assume a configuration in which they react with antibodies, in the same manner as they do in vivo. As illustrated by the decompositions of binding shown in Tables 2 to and 3A to 3C (FIGS. 10-13), this encoding design can allow one to distinguish among antibodies directed to eight proteins or peptides, P1 to P8, or certain combinations thereof.

Number Coding under Uncertainty—Were carriers of each subtype identical, and experimental conditions perfect, then signals from each carrier of a given subtype would be identical, histograms of signal intensities recorded from instances of each subtype would contain δ-function peaks, and subtypes would be discriminated merely by ensuring, for the pair, $w:=n_C^W \neq v:=n_C^V$, or, for multiplets, a unique numerical decomposition. In practice, however, signals from nominally identical carriers display a finite variance, resulting, for example, from the chemical heterogeneity of carriers, statistical fluctuations in analyte capture to carrier-displayed probes and noise in signal acquisition. Under such conditions, exceptionally high signals recorded from nominally "negative" carriers may exceed exceptionally low signals recorded from nominally "positive" carriers, producing overlap of peaks for the W and V alleles in a histogram of intensities recorded from all carriers of a particular code, e.g., type C.

Confidence Intervals—A finite variance in assay signals recorded from carriers of different type will of course affect the reliability of discrimination between W and V alleles regardless of the method of coding. Thus, the standard methods of statistical analysis apply to the construction of confidence intervals—once the step of partitioning of the carrier population into types has been accomplished.

For example, if carriers for W and V probes were color coded, the construction of confidence intervals would proceed by the usual standard methods of statistical analysis, applied to intensities, $I_{W1}, I_{W2}, \ldots, I_{Ww}$ recorded from the w carriers displaying the W-probe and to intensities, $I_{V1}, I_{V2}, \ldots, I_{Vv}$ recorded from the v carriers displaying the V-probe. These sets of intensities yield mean values, Overline$\{I_W\}$ and Overline$\{I_V\}$, with the respective variances, $S_w^2$ and $S_v^2$. Under the assumption that the w and v intensities in the two sets represent independent observations, the t-distribution provides an expression relating the values (w, Overline$\{I_W\}$, $S_w^2$) and (v, Overline$\{I_V\}$, $S_v^2$) to the desired probabilities that confidence intervals constructed from the two sets of observations and placed on the mean values of the observed intensities contain the true mean values $<I_W>$ and $<I_V>$. Alternatively, the t-distribution can be applied in this circumstance to test whether the means of the two intensity populations are the same (or not) (see e.g., Chapt. 9 in "Principles of Statistics", M. G. Bulmer, Dover Publications, 1979, incorporated by reference).

The construction of a desired confidence interval to be placed on mean values requires a minimal number of observations, or here, a minimal number of carriers of each type, thereby setting a lower bound on w and v. Stated otherwise, decreasing the number of beads for a given CV and mean value increases the confidence interval.

Figure 8:
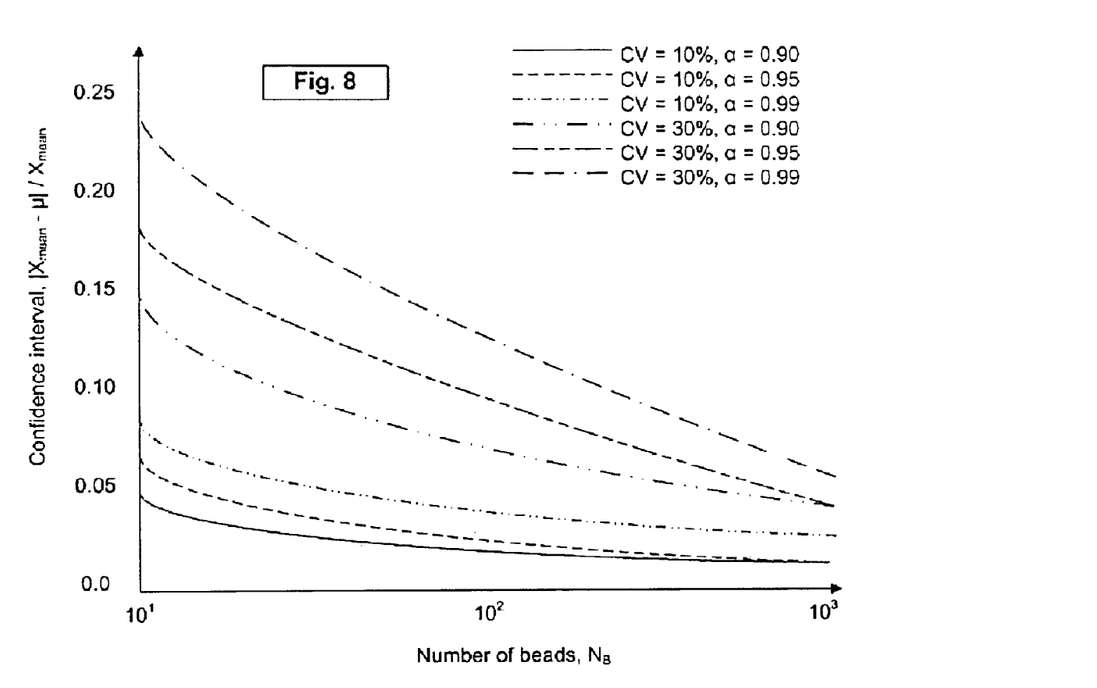
FIG. 8 is a plot of confidence interval against number of beads, at different CVs and significance levels (α).

FIG. 8 shows the confidence interval for cases where the assay CV is 10% and 30%. The interval defining the range of the calculated mean is plotted against the minimum number of beads $N_B$ necessary for significance levels of 90%, 95% and 99%. A larger number of beads ensures that the confidence interval is smaller.

Partitioning—In contrast to other encoding methods such as C-coding, N-coding is subject to additional uncertainty as a result of peak overlap and equivalent ambiguities affecting recorded assay signal intensities. Thus, referring to N-coding of pairs in the context of mutation analysis, partitioning into + and − subtypes may not be obvious by mere inspection of the data, as presumed in the Count-Compare-Confirm procedure of determining subtypes.

In such a circumstance, the partitioning step may be performed by introducing a suitable optimality criterion, assuming, for the moment, that $w:=n_C^W$ and $v:=n_C^V$ are known, for example, by explicit counting of carriers of each subtype prior to pooling. While described here for a pair of subtypes, the partitioning process is readily generalized to the discrimination of other than pairs by considering two or more thresholds in the partitioning step in accordance with the known instances for each possible subtype.

---

Construct a histogram of intensities recorded from all carriers sharing one C-code;
    IF (histogram has only a single peak such that :
        n+/(w + v) ~ 1) THEN: H
    ELSE find an optimal threshold, τ, such that:
        (n+(τ) − w)^2 = min AND (n− (τ) − v)^2 = 
        min THEN: W allele
    OR
        (n+(τ) − v)^2 = min AND (n− (τ) − w)^2 = 
        min THEN: V allele
wherein n+(τ) and n−(τ) are obtained by integration over the two partitions produced by partitioning of the histogram in accordance with the selection of the threshold T.

---

Figure 5:
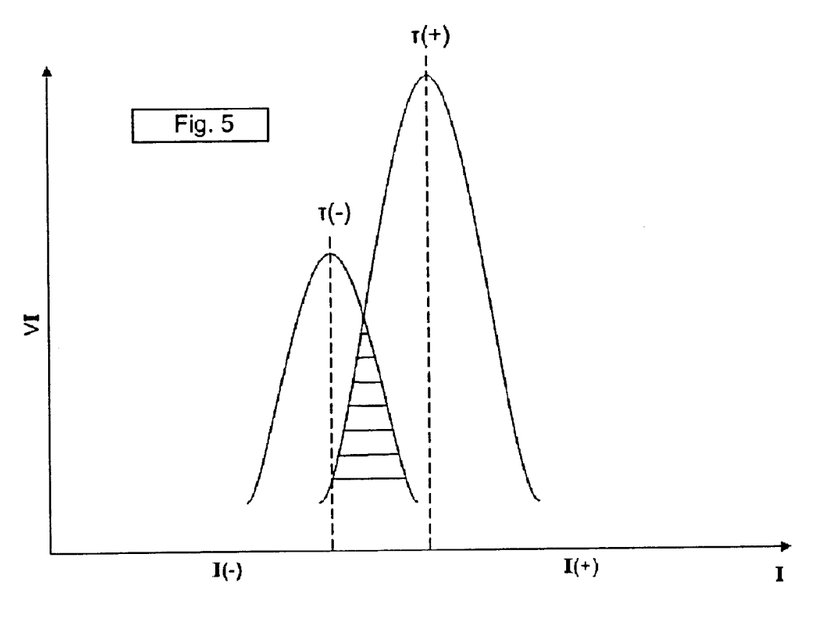
FIG. 5 depicts a plot of results as show in FIG. 4, but for overlapping histogram peaks in this case.

In the event of peak overlap, the experimentally recorded numbers $p:=n+(T)$ of "positive" intensities, $I_1^+, I_2^+, \ldots, I_p^+$ and $n:=n-(T)$ of "negative" $I_1^-, I_2^-, \ldots, I_n^-$, will depend on the threshold T. For example, exceptionally low signals recorded from nominally "positive" carriers may exceed exceptionally high signals recorded from nominally "negative" carriers, and once a threshold is selected, a certain number of "false negatives" and "false positives" will result. That is, carriers whose assay signal intensities fall into the peak overlap region may be assigned incorrect codes. The numbers p and n will then differ from the numbers w of particles displaying a probe matching the W-allele and v of particles displaying a probe matching the V-allele. Accordingly, to ensure robust N-coding, the choice of w and v must be such that peak overlap will not corrupt the code (FIG. 5).

A first condition ensuring robust N-coding may be based upon the observation that the maximal number, e, of errors in carrier type assignments will result when all errors either are false negatives, n→n+e, p→p−e, or false positives, n→n−e, p→p+e, and that this maximal number will be an increasing function of the magnitude of peak overlap, $\Sigma$: $e=e(\Sigma)$. That is, extreme values of the threshold, T, either to the right extreme of the overlap region or to the left extreme of the overlap region will produce the greatest deviations in n and p (FIG. 5).

Thus, a conservative criterion guiding the selection of w and v can be stated as follows:

---

IF (without overlap: p > n)      THEN ensure p − e > n + e
                                                      with overlap.
ELSE IF (without overlap: p < n)     THEN ensure p + e < n − e
                                                      with overlap

---

To ensure that these conditions are met, N-coding is preferably used only when it can be ensured that the N-coded subtypes produce substantially different assay signal intensities, thereby minimizing peak overlap.

That is, N-coding in accordance with the present invention preferably is used to represent discrete outcomes of an assay such that overlap between partitions in an intensity histogram is negligible. This is ensured by employing N-coding to represent assay outcomes only when the observed mean assay signal intensities are separated by at least one standard deviation, and preferably three standard deviations, to minimize the maximal number of possible false negatives or false positives. Alternatively, if a peak overlap of magnitude $\Sigma$ is anticipated, w and v must be chosen in accordance with a design criterion such as the one stated above.

Number Fluctuations—In addition to accounting for experimental uncertainty in the determination of the values of p and n, allowance also must be made for statistical uncertainty regarding the values w and v themselves. Such uncertainty can arise as a result of fluctuations in the number of particles contained in aliquots (of nominally identical volume) that are prepared in the course of practicing the invention.

For example, if, as in READ™, carriers are placed into a random array in a designated area of a planar substrate, fluctuations in the number of each carrier subtype included in the array are expected to be in accordance with a certain probability distribution whose mean is related to the concentration of the carrier reservoirs, preferably maintained in the form of a stable suspension, as described in Example 3.

Figure 6:
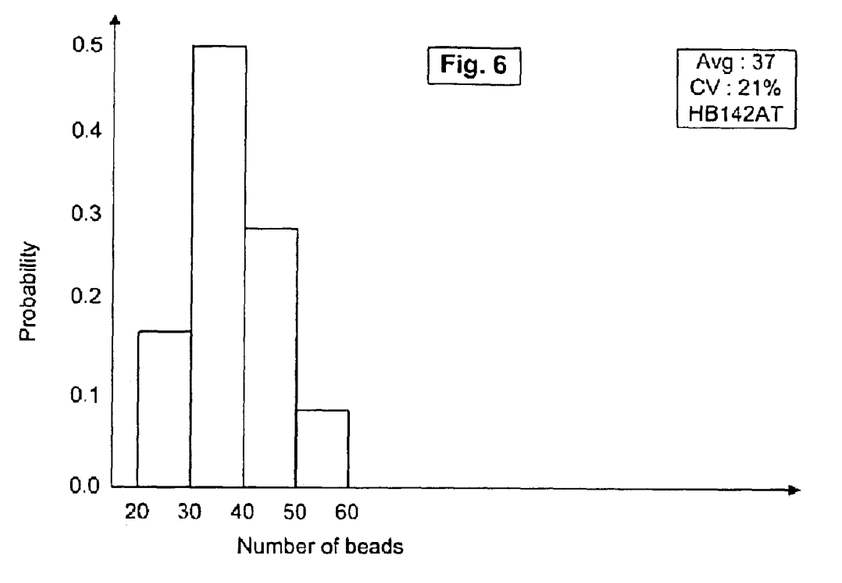
FIG. 6 is a histogram representing the probability of selecting a given number of carriers ("beads") of particular types of 70 subtypes, based on the evaluation of 40 random encoded arrays of beads, where the anticipated number of beads of each type was about 60. A total of about 3,500 beads (of 70 types) are anticipated to be present in each of the 40 bead arrays, based on an average 90% occupation of available sites. For each type, the CV was calculated over the population of 40 arrays evaluated.
Figure 7:
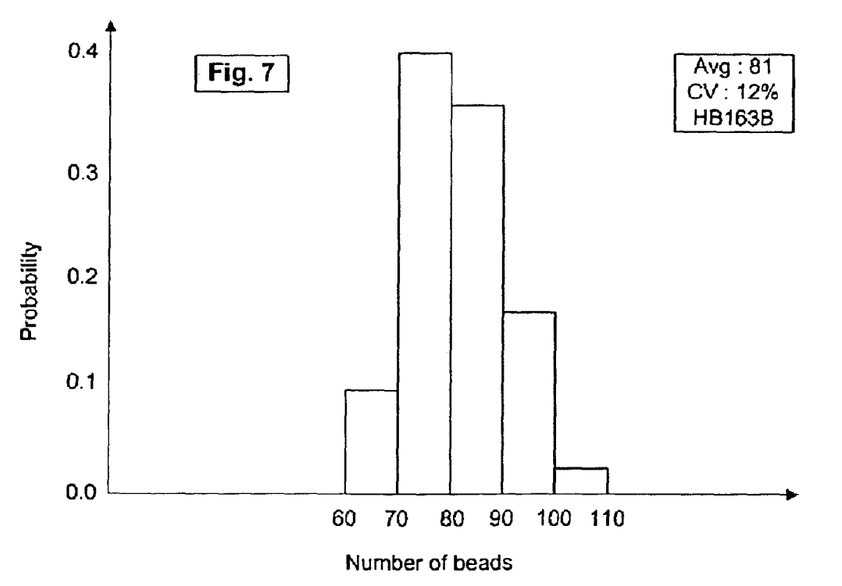
FIG. 7 is a histogram plot as in FIG. 6, but for another type of beads.

Accordingly, actually realized values of w and v are determined only to within a certain range of possible values, namely $w^*=w\pm\delta w$ and $v^*=v\pm\delta v$, as shown by comparison of FIGS. 6 and 7, and allowance must be made for this uncertainty in the selection of the design values for w and v. For example, in the case of Poisson statistics, $\delta w \sim \langle w \rangle$, $\delta v \sim \langle v \rangle$, i.e., significant deviations of w and v are possible. Thus, a necessary condition to be satisfied by a robust N-code may be stated as follows:

---

IF (N-code is to ensure v* < w*) :
    THEN select v, w such that v + δv < w − δw
ELSE IF (N-code is to ensure v* > w*) :
    THEN select v, w such that v − δv > w + δw

---

In addition to this condition, a robust N-code also must take into account experimental uncertainties such as those discussed above which may affect the observed counts, p and n. Thus, a more general criterion guiding the selection of w and v can be stated as follows:

```
IF (N-code is to ensure (|p−w*| < |p−v*|) AND
   (|n−v*| < |n−w*|)    /* W
allele */
       THEN ensure    max{|p±e − w*|} < min{|p±e − v*|}AND
                      max{|n±e − v*|} < min{|n±e − w*|}
   ELSE IF (N-code is to ensure (|p−v*| < |p−w*|) AND
   (|n−w*| < |n−v*|) /* V
allele */
       THEN ensure    max{|p±e − v*|} < min{|p±e − w*|} AND
                      max{|n±e − w*|} < min{| n±e − v*|}
```

These multiple conditions to be placed upon a proper choice of w and v for robust N-coding restrict the practical use of N-coding as a general encoding methodology, as discussed at the outset. N-coding is then particularly useful in connection with a color code ("C-code") because it reduces the set of color codes required for encoding of a given number of probes. For example, for the ACMG panel of 25 CF mutations requiring, instead of 50 color codes, only 25 color codes are required. Conversely, N-coding extends by a factor of two the coding complexity of a given set of color codes, thereby facilitating the process of manufacturing sets of color-encoded particles. Therefore, provided that N codes are constructed in accordance with the design rules outlined above, N coding can be used as part of a coding system involving color or other encoding markers, for certain of the carriers in a larger group, where such carriers are encoded identically but for their number codes.

EXAMPLES

Example 1

N-Coding of eMAP Probes for Detection of ΔF 508 CF Mutation

Mutation analysis was performed by placing members of a probe pair, designed to detect wild type and the ΔF 508 cystic fibrosis ("CF") mutation on beads of the same color, but selecting different numbers of V-beads and W-beads. Assay results were analyzed by recording signal intensities indicating hybridization of probe and target, and by analyzing these results in accordance with the histogram representation and CCC procedure described herein.

Protocols—Wild type (W) and mutant (V) probes relating to the ΔF 508 CF mutation fixed to beads of the same color, and beads were pooled at different ratios of W to V probes and assembled into planar arrays in accordance with the READ™ format. On a first chip, the ratio of W:V was 1:5, and on a second chip the ratio of W:V was 5:1.

For detection of hybridization of probe and target, an elongation assay ("eMAP" see U.S. application Ser. No. 10/271,602, filed Oct. 15, 2002, incorporated by reference) was used. Known wild type and ΔF 508 heterozygous samples were applied to both types of chips, and histograms were generated. See FIGS. 1A to 1D.

Bead Functionalization

Aliquots of a suspension of a bead designated G3H (a blue-green tosylated bead modified with Bovine Serum Albumin ("BSA") in accordance with the methods disclosed in a co-pending application was functionalized with each of the following amino-modified DNA probes:

508W: Sequence: GGC ACC ATT AAA GAA AAT ATC ATC (SEQ ID NO. 1)

ΔF 508: Sequence: GGC ACC ATT AAA GAA AAT ATC ATT (SEQ ID NO. 2)

The following protocol was used to attach these probes to the BSA-modified beads.

BSA Protocol
1. Add 100 μL of beads to a tube containing 500 μL PBST, mix with vortex
2. Centrifuge for 1 min and remove the supernatant
3. Add 500 μL MES (0.1M, pH 4.5), mix with vortex,
4. Centrifuge for 1 min and remove supernatant
5. Prepare 0.05M of EDAC in MES right before use:
    a. Take EDAC out of freezer and let it warm to room temperature for 30 min
    b. Add 4 mL of MES (0.1M, pH 4.5) to 40 mg EDAC, mix with vortex
6. Add 500 μL of EDAC solution to each tube of beads
7. Add 10 μL probe (100 μM) to each bead suspension
8. Allow the beads to react for 1 hour at room temperature with end-over-end mixing
9. Add 100 μL of PBST to each tube after reaction, mix with vortex, centrifuge for 1 min, and remove supernatant
10. Wash beads twice with 500 μL of PBST and resuspend the beads in 100 μL of TBS-2.

Bead Pooling:

Two pools were prepared using beads functionalized with 508W and ΔF 508 probes, as well as beads modified with OligoC (negative control) and probes matching beta-actin (positive control). In Pool A, the ratio of 508WT to F508 was 1:5, while in Pool B, the ratio was 5:1.

The following pooling protocol was used:
1. Add each of the four modified beads to an empty tube according to the volumes noted below
2. Wash beads once in 100 μL 10 mM Tris
3. Resuspend beads in 36 μL 10 mM Tris

| Bead | Volume added (μL) |
| --- | --- |
| Pool A: | |
| G3H-508WT | 1 |
| G3H-F508 | 5 |
| G4B-OligoC-2 | 15 |
| G1E-BA | 15 |
| Pool B: | |
| G3H-508WT | 5 |
| G3H-F508 | 1 |
| G4B-OligoC-2 | 15 |
| G1E-BA | 15 |

Assembly of Random Encoded Bead Arrays

A total of four arrays were assembled on the upper surface of a substrate (a "chip"), where two of these arrays were composed of Pool A, and the other two were composed of Pool B.

Elongation Assay

For the elongation, 6.5 μL PCR product was extracted from known WT or M samples and placed into a PCR tube, to which 2 μL Exo-sap was added. The mixture was incubated at 37° C. for 25 min and 80° C. for 15 min (in a thermocycler). Thereafter, λ exonuclease was used for digestion into single stranded DNA. The reaction mixture included each of: dGTP, dTTP, dATP and dCTP. Following PCR amplification, the following Ex-10 primers were used in multiplexed PCR:

SEQ ID NO. 3  GGC GTC CCA AAA GGG TCA GTG AGC CTT
              CAG AGG GTA AAA T:

-continued

Figure 1A:
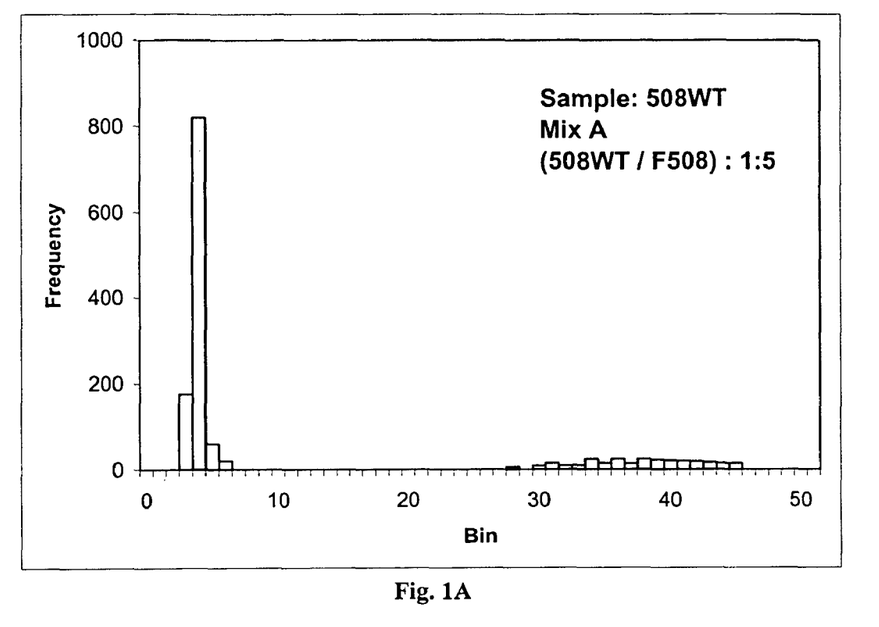
FIGS. 1A to 1D show assay results of numerical coding for detecting the F508 mutation using elongation detection, in the form of a series of four histograms, where, in each histogram, the number of beads displaying a signal of a certain intensity is plotted against intensity.

SEQ ID NO. 4 GCG GTC CCA AAA GGG TCA GTC AGT AGC
        TTA CCC ATA GAG G:

The results of the assay are shown in FIGS. 1A to 1D, in the form of a series of four histograms. In each histogram, the number of beads displaying a signal of a certain intensity is plotted against intensity. In FIG. 1A, a wild-type ("W") sample is added to a bead pool in which the ratio of the number of beads functionalized with probes complementary to the W subsequence to that of beads functionalized with probes complementary to the variant ("V") is 1 to 5. The histogram has two peaks, but, as expected, the peak corresponding to the beads producing a positive signal has only a small area, indicating that only a small number of beads produce a positive signal.

Figure 1B:
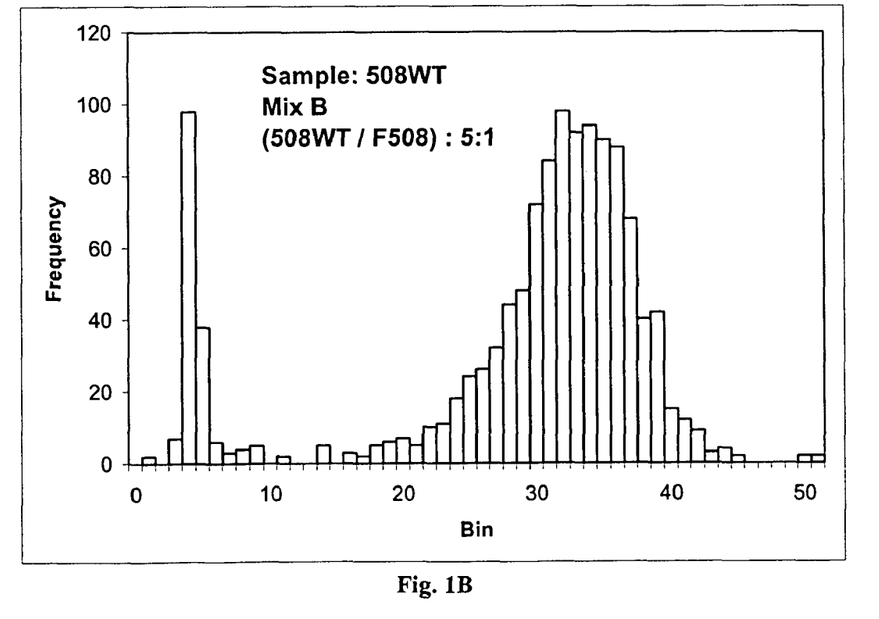
Figure 1C:
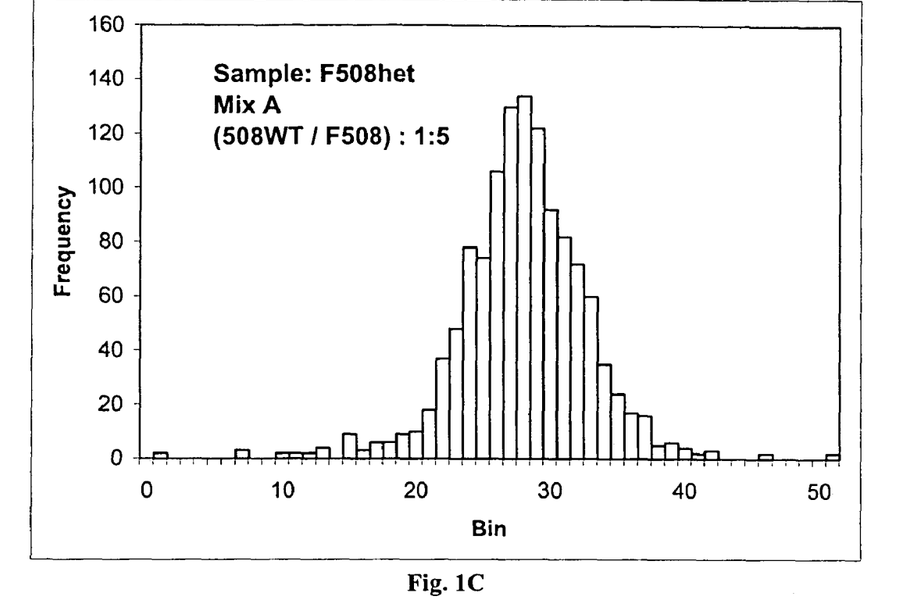
Figure 1D:
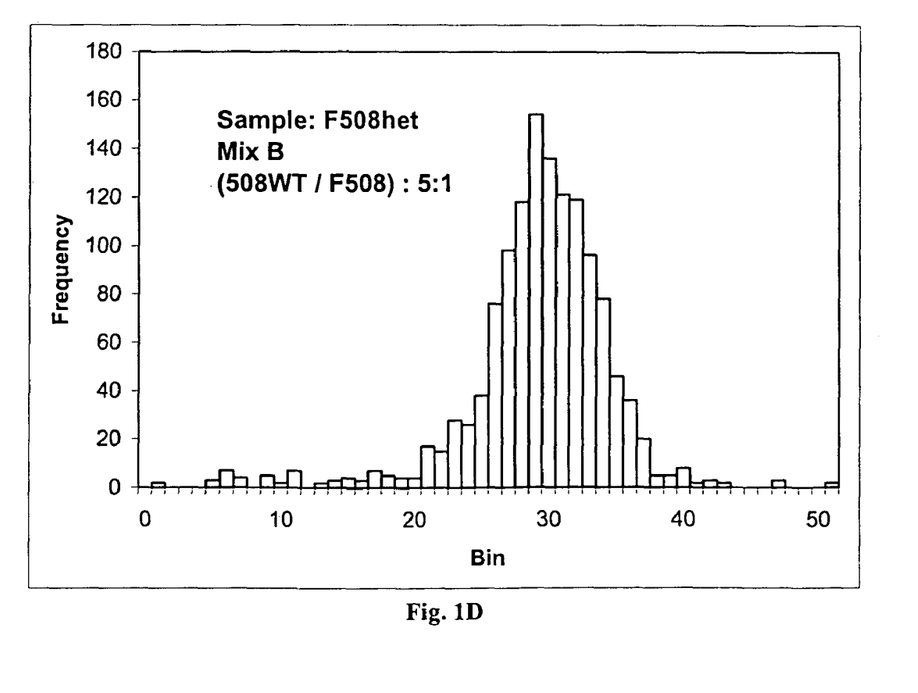
Figure 2:
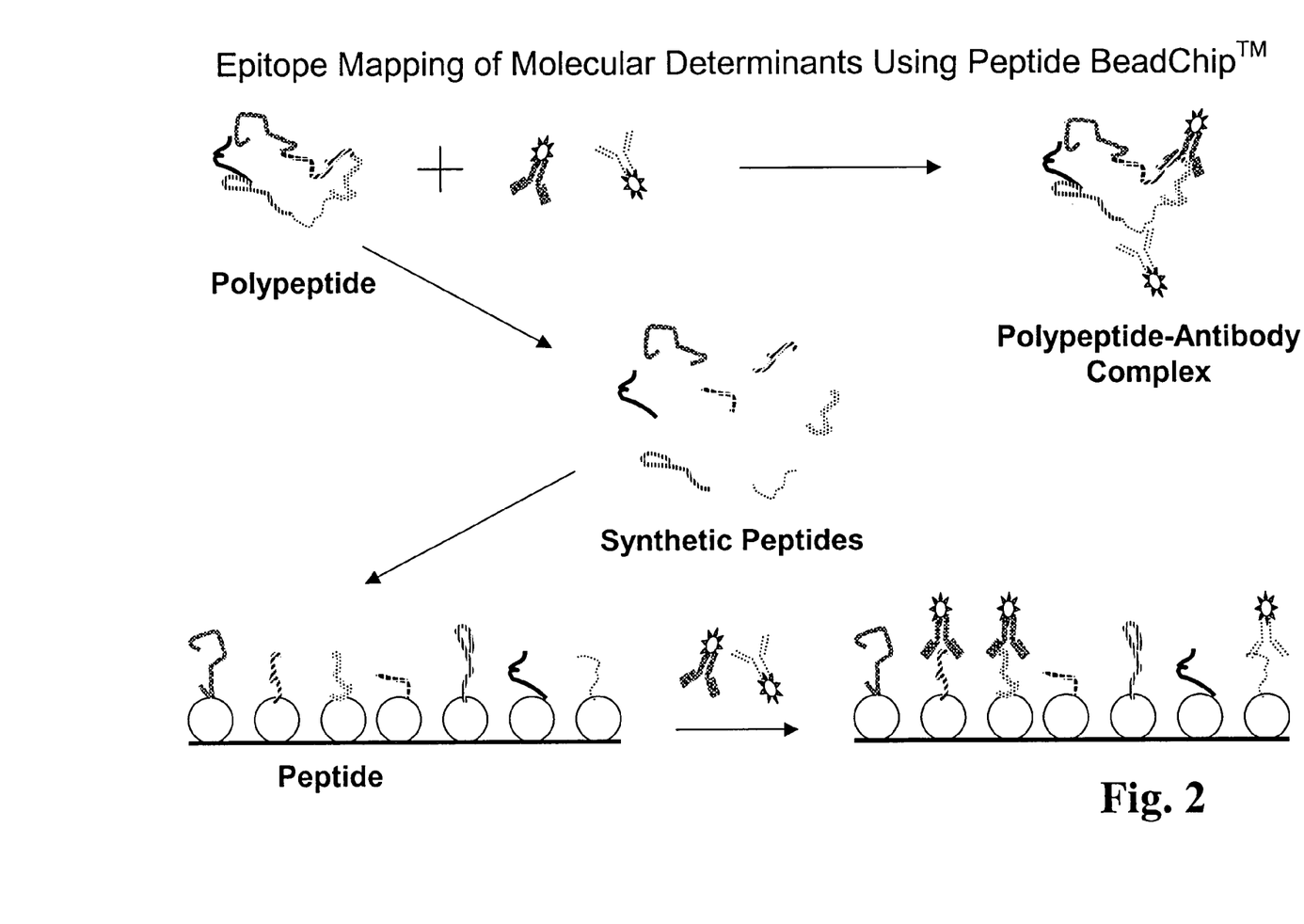
FIG. 2 depicts the native conformation of a protein which can be bound to either of two antibodies; the generation of synthetic peptide fragments corresponding to different linear epitopes of the protein and attaching the fragments to beads; and, the binding of labeled antibodies to the peptide fragments on the beads. A labeled secondary antibody could be used for detection, if the peptide fragments were initially bound by an unlabeled antibody (not shown).

In FIG. 1B, the sample is the same, but the ratio of beads of each type is reversed, and, as expected, the reverse ratio of peak areas is observed in the histogram. In FIG. 1C and 1D, the sample is heterozygous for W and V, and, as expected, irrespective of the ratio of V and W, a large number of beads produce a positive signal.

Example 2

Detecting Auto-Antibodies

Figure 9:
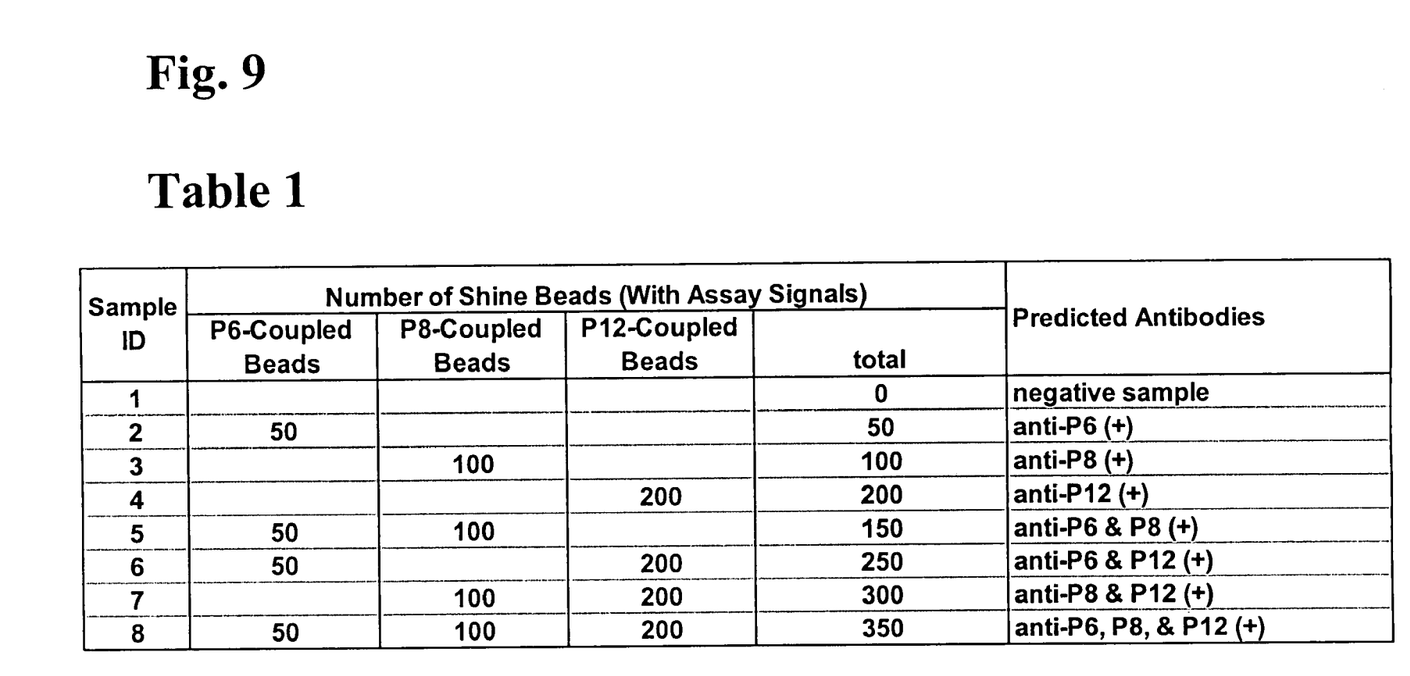
FIG. 9 is Table 1, showing results from three synthetic peptides P6, P8, and P12 affixed to the same colored microspheres in separate reactions.
Figure 10:
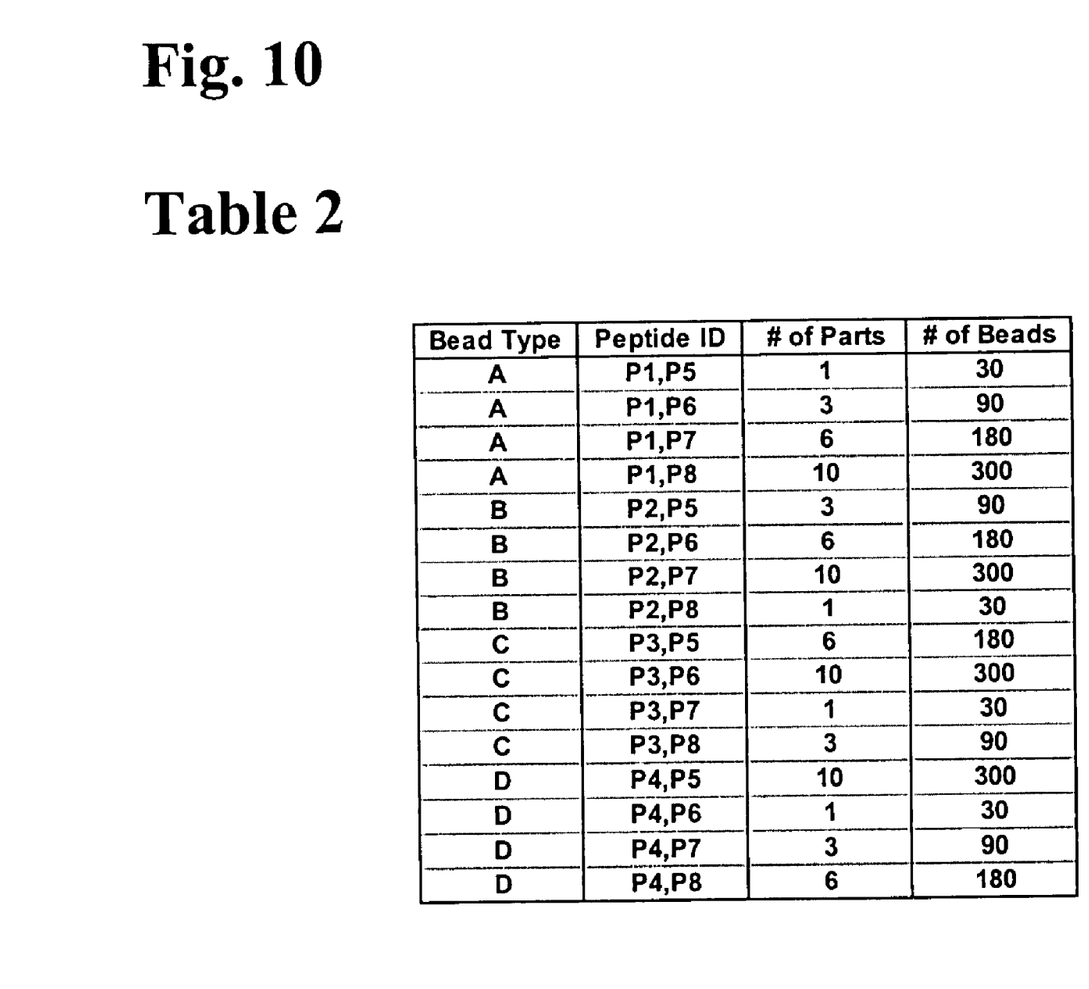
FIG. 10 is Table 2, showing bead types with different peptide pairs associated with beads.
Figure 11:
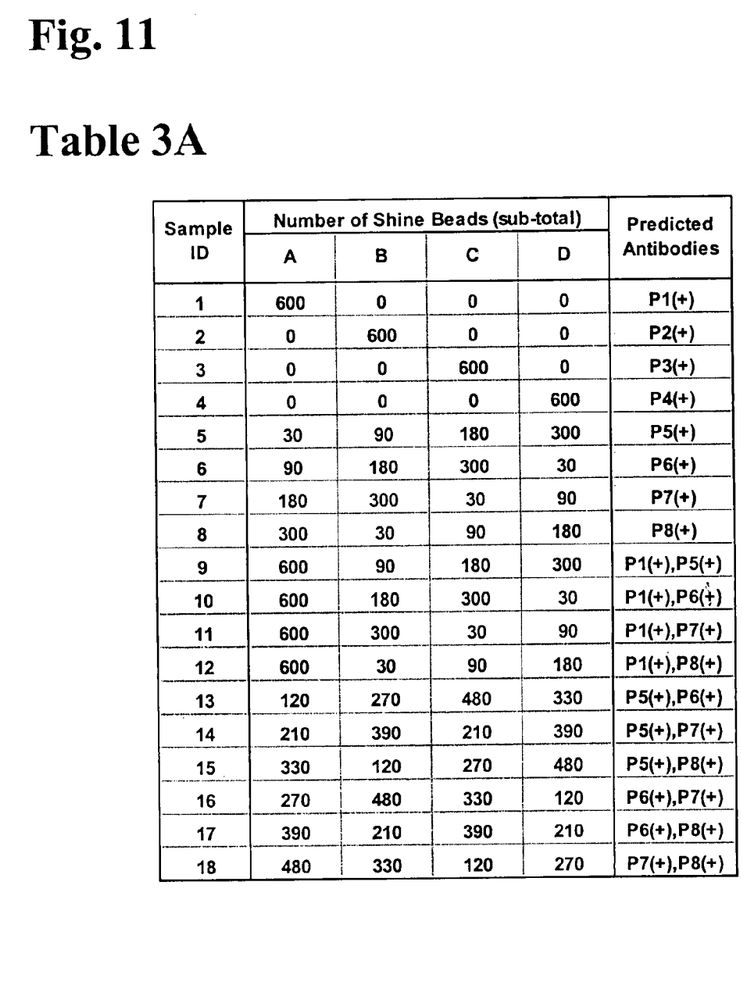
FIG. 11-13 are, respectively, Table 3A to 3C, showing beads reactive with different samples.
Figure 12:
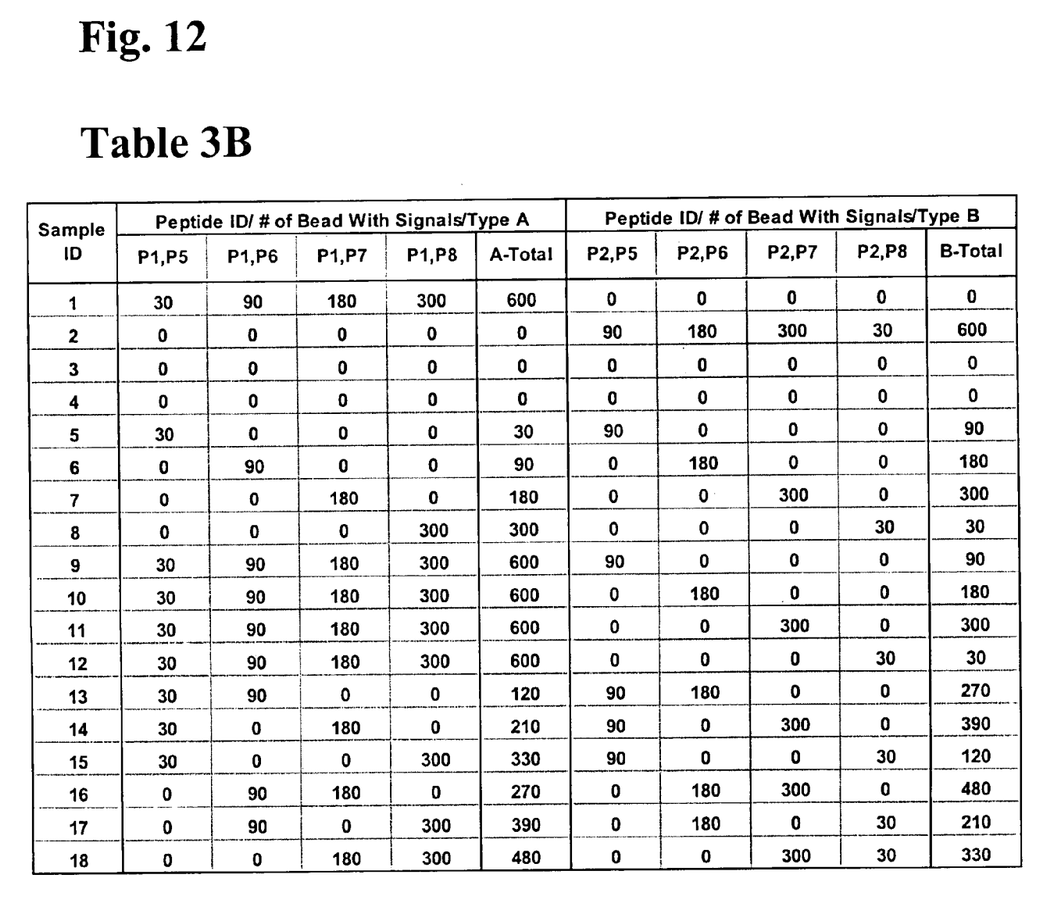
Figure 13:
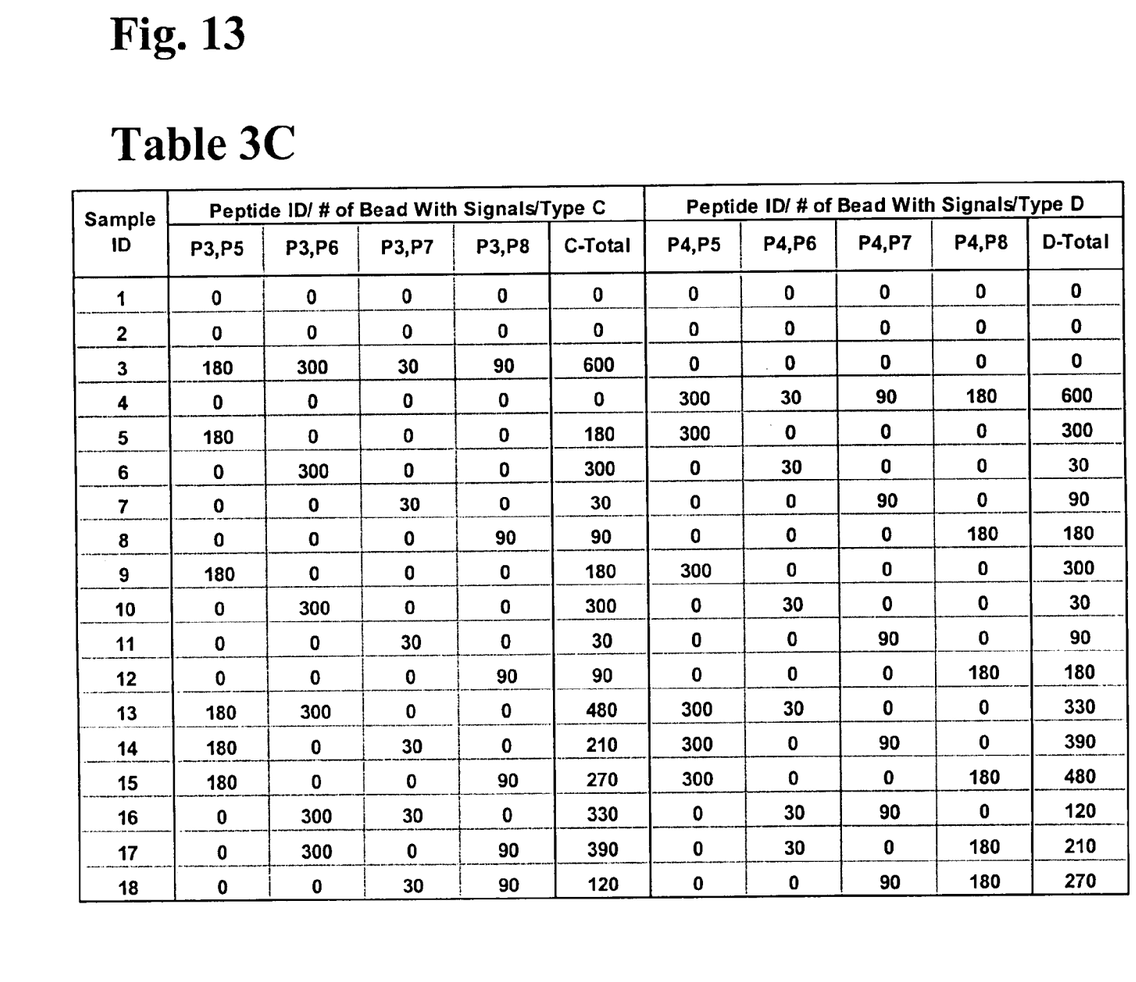

As shown in Table 1 (FIG. 9), three synthetic peptides P6, P8, and P12 are affixed to the same colored microspheres in separate reactions. These synthetic peptides are biotinylated at their N-termini with an 18-carbon spacer and immobilized by way of biotin-neutravidin complex formation. Beads are pooled, for example, at ratios of one part of P6-functionalized beads, two parts of P8-functionalized beads, and four parts of P12-functionalized beads and an array is assembled on the surface of a silicon chip (Beadchip™).

Beadchips were incubated in separate experiments with two 1:20 diluted serum samples positive for antibody directed against a lupus characteristic antigen, SCL-70 (#1764 from BiosPacific and #68933 from METIC Lab. After removing non-reacted antibodies, specific antibodies captured by the peptides were visualized using a fluorescently labeled goat-anti-human IgG antibody-conjugate. Decoding and assay images were acquired using a microscope equipped with a CCD camera, as in the previous example. The assay signals were extracted, and the Pi/P7 ratios (peptide-specific signal intensity vs. the signal intensity of negative control peptide, P7) were calculated. Beads with an intensity value significantly higher than that of the negative control were designated positive.

The presence of P6, P8 or P12-specific antibodies was determined by the relative numbers of positive beads. As shown in Table 1 (FIG. 9), assaying sample #1764 yielded 300 positive beads, meaning the positive beads captured anti-P8 (100 positive beads) and anti-P12 (200 positive beads) antibodies. Sample #68933 yielded 150 positive beads, meaning the positive beads captured anti-P6 (50 positive beads) and anti-P8 (100 positive beads) antibodies.

Example 3

Number Fluctuations in Random Encoded Bead Arrays

To prepare a pool of 50 types of encoded carriers in the form of polymer microparticles ("beads") of 3 μm diameter, 50 μl aliquots of each bead type are taken from a reservoir containing 1 ml of a stable suspension and split in order affix to each particle of a specific type a selected chemical entity such as an oligonucleotide probe. Next, 5 μl aliquots of probe-functionalized beads are taken from each reaction container and pooled to produce 250 μl of suspension containing 50 types of functionalized beads. Finally, in accordance with the Random Encoded Array Detection (READ) format, a 0.5 μl aliquot of pooled bead suspension is placed onto a planar silicon substrate, covering an area of approximately 1 mm$^2$ which includes a designated area of 300 μm by 300 μm, thus approximately 10% of the total area, for assembly of a planar array of 4000.

Under these assumptions about the relative size of aliquot ("sample") and reservoir, and about the relative size of designated area and total area of substrate, bead types will be distributed about the mean value, say the average density of particles in the original volume of suspension, in accordance with a Poisson distribution such as those shown in FIGS. 6 and 7.

The terms, expressions and examples hereinabove are exemplary only, and not limiting, and the invention is defined only in the claims which follow and includes all equivalents of the subject matter of the claims. Unless otherwise indicated, steps in method claims can be performed in any order, including but not limited to the order set forth in the claims.

What is claimed is:

1. A method of genotyping a nucleic acid sample using pairs of solid phase carriers, where members of a particular pair display a probe having a subsequence complementary to one of two different target subsequences, wherein said two different target subsequences differ from each other at one position and wherein at least some of said target subsequences, individually or together, are present in a nucleic acid sample amplified from a eukaryotic organism, and where the number of members displaying each said probe subsequence is known, comprising:

reacting the nucleic acid sample with the members of the pairs of solid phase carriers such that a positive signal is generated upon reaction of a target subsequence with its complementary probe; and determining whether the target nucleic acid sample is homozygous for either of the subsequences, or is heterozygous by applying the formulas below:

where $=n_c^v$ equals the number of carriers carrying the probe complementary to one of two different target subsequences, and $n_c^w$ equals the number of carriers carrying the probe complementary to the other of said two different target subsequences, and $n_c+$ is the total number of the carriers which carry a positive-signal following said reaction, then:

when $n_c+/n_c^w \approx 1$; the sample is homozygous for the one subsequence (designated W);

when $n_c+/n_c^v \approx 1$; the sample is homozygous for the other subsequence (designated V); and when $n_c+/(n_c^v+n_c^w) \approx 1$; the sample is heterozygous.

2. The method of claim 1 wherein following reaction with the nucleic acid sample, the number of members failing to generate a positive signal are counted and designated $n_c-$, and $n_c-$ is used to confirm whether the target sample is homozygous or is heterozygous.

3. The method of claim 2 further comprising confirming or refuting the determination that the target nucleic acid sample is homozygous for either of the subsequences, or is heterozygous, by performing the following steps, as indicated:

where the method of claim 1 indicates the sample is homozygous for W:

$n_c-/n_c^v \sim 1$;

where the method of claim 1 indicates the sample is homozygous for V:

$n_c-/n_c^w \sim 1$; or where the method of claim 1 indicates the sample is heterozygous:

$n_c-/(n_c^w+n_c^v) \sim 0$.

4. The method of claim 1 wherein the carriers are beads.

5. The method of claim 1 wherein the positive carriers are determined by performing an assay-detecting hybridization of labeled target to probes, or by performing an assay in which hybridization of the probe and target sample is followed by elongation to label the probe.

6. The method of claim 5 in which positive carriers are identified by detecting an optical signal.

7. The method of claim 1 wherein carriers displaying probes having different subsequences are differently encoded.

8. The method of claim 7 wherein the encoding is by color.

* * * * *

SEQUENCE LISTING

```
<160> NUMBER OF SEQ ID NOS: 4

<210> SEQ ID NO 1
<211> LENGTH: 24
<212> TYPE: DNA
<213> ORGANISM: Artificial Sequence
<220> FEATURE:
<223> OTHER INFORMATION: Artificial Probe

<400> SEQUENCE: 1
ggcaccatta aagaaaatat catc                                          24

<210> SEQ ID NO 2
<211> LENGTH: 24
<212> TYPE: DNA
<213> ORGANISM: Artificial Sequence
<220> FEATURE:
```

```
<223> OTHER INFORMATION: Artificial Probe

<400> SEQUENCE: 2
ggcaccatta aagaaaatat catt                                          24

<210> SEQ ID NO 3
<211> LENGTH: 40
<212> TYPE: DNA
<213> ORGANISM: Artificial Sequence
<220> FEATURE:
<223> OTHER INFORMATION: Artificial Primer

<400> SEQUENCE: 3
ggcgtcccaa aagggtcagt gagccttcag agggtaaaat                         40

<210> SEQ ID NO 4
<211> LENGTH: 40
<212> TYPE: DNA
<213> ORGANISM: Artificial Sequence
<220> FEATURE:
<223> OTHER INFORMATION: Artificial Primer

<400> SEQUENCE: 4
gcggtcccaa aagggtcagt cagtagctta cccatagagg                         40
```